United States Patent
Spoor et al.

(10) Patent No.: US 8,504,309 B1
(45) Date of Patent: Aug. 6, 2013

(54) SYSTEMS AND METHODS FOR EVALUATION OF OBJECT CONDITION

(75) Inventors: Todd Alan Spoor, Los Angeles, CA (US); John Ambrose Mulcahy, St. Thomas, VI (US); Scott Stanaway McCrae, Potomac Falls, VA (US); Kevin Francis Cassidy, Leesburg, VA (US)

(73) Assignee: Movie Poster Grading and Registry Company, LLC, Los Angeles, CA (US)

( * ) Notice: Subject to any disclaimer, the term of this patent is extended or adjusted under 35 U.S.C. 154(b) by 220 days.

(21) Appl. No.: 12/914,521

(22) Filed: Oct. 28, 2010

(51) Int. Cl.
*G01B 5/28* (2006.01)

(52) U.S. Cl.
USPC .............................................. 702/35; 702/34

(58) Field of Classification Search
USPC ..................................................... 702/34, 35
See application file for complete search history.

(56) References Cited

U.S. PATENT DOCUMENTS

| | | | |
|---|---|---|---|
| 4,441,943 A | 4/1984 | Kydd | |
| 4,880,750 A | 11/1989 | Francoeur | |
| 4,899,392 A * | 2/1990 | Merton | 382/136 |
| 5,139,812 A | 8/1992 | Lebacq | |
| 5,194,289 A | 3/1993 | Butland | |
| 5,220,614 A * | 6/1993 | Crain | 382/136 |
| 5,360,628 A | 11/1994 | Butland | |
| 6,612,494 B1 | 9/2003 | Outwater | |
| 7,113,620 B2 * | 9/2006 | Shiotani | 382/112 |

* cited by examiner

*Primary Examiner* — Sujoy Kundu
*Assistant Examiner* — Harun Chowdhury
(74) *Attorney, Agent, or Firm* — Rossi, Kimms & McDowell LLP

(57) ABSTRACT

A condition of an object is evaluated with improved uniformity as compared to conventional schemes. For example, flaw types and severities associated with flaws potentially present in a certain category of objects are predefined, along with rules for evaluating the condition of objects of the certain category based at least on the flaw types and severities. In this manner, any user, expert or not, can uniformly evaluate the condition of an object merely by identifying and inputting the flaws according to the predefined flaw types and severities. In addition, the predefined flaw types, severities, and rules can be changed by a user or otherwise at any time, and different sets of predefined flaw types, severities, and rules can be generated for each of a plurality of different categories of objects, thereby providing a fully configurable and flexible evaluation system.

45 Claims, 8 Drawing Sheets

Weighting Factor Database 500

| Flaw Type | Severity Type | Size | Location | Weighting Factor |
|---|---|---|---|---|
| Fold Line | Some Wear | | | 20 |
| Fold Line | Heavy Wear | | | 200 |
| Fold Line | Separation | 0.25" | | 50 |
| Fold Line | Separation | 0.5" | | 60 |
| Tear | | 0.25" | Border Area | 10 |
| Tear | | 0.5" | Border Area | 20 |
| Tear | | 0.25" | Image Area | 15 |
| Tear | | 0.5" | Image Area | 30 |

*FIG. 5*

| Flaw No. | Flaw Type | Severity Type | Size | Location | Weighting Factor |
|---|---|---|---|---|---|
| 1 | Fold Line | Some Wear | | | 20 |
| 2 | Fold Line | Heavy Wear | | | 200 |
| 3 | Tear | | 0.25" | Image Area | 15 |

*Cumulative weighting factor for the Fold Line flaw type is 220*

FIG. 6

Grading Matrix 700

| Grade # | Grade Name | Fold Line | Tear |
|---|---|---|---|
| 10.0 | Mint | 10 | 0 |
| 9.5 | Near Mint | 20 | 10 |
| 9.0 | Very Fine + | 120 | 30 |
| 8.5 | Very Fine | 200 | 40 |
| 8.0 | Very Fine - | 300 | 40 |
| 7.5 | Fine + | 400 | 80 |
| 7.0 | Fine | 500 | 130 |
| 6.5 | Fine - | 600 | 240 |
| 6.0 | Very Good + | 720 | 310 |
| 5.5 | Very Good | 840 | 310 |
| 5.0 | Very Good - | 960 | 480 |
| 4.5 | Good + | 1100 | 600 |
| 4.0 | Good | 10000 | 750 |
| 3.5 | Good - | 10000 | 900 |
| 3.0 | Fair + | 10000 | 1100 |
| 2.5 | Fair | 10000 | 1300 |
| 2.0 | Fair - | 10000 | 1600 |
| 1.0 | Poor | 1000000 | 1000000 |

Fold Line flaw type is most harmful because it results in the lowest Grading Matrix Score (8.0 vs. 9.0 for the Tear flaw type)

FIG. 7

SYSTEMS AND METHODS FOR EVALUATION OF OBJECT CONDITION

COPYRIGHT NOTICE

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD

This invention relates to evaluating objects, such as manmade artifacts or naturally occurring objects. In this regard, some embodiments of the present invention pertain to evaluating objects based at least on an evaluation of flaws present in an object and a severity of each of the flaws.

BACKGROUND

Conventionally, evaluation of objects has been performed by experts in the respective fields to which the objects belong. Such experts rely upon their many years of experience to evaluate the condition of an object and, often times, assign a grade, such as "mint", "good", "fair", or "poor" to the object to indicate its condition. However, having the same object evaluated by different experts in the same field often times results in different grades for the object due to differing opinions between the experts and different evaluation criteria used by the experts.

Accordingly, having an object evaluated by experts often is time consuming due to the manual labor required by the experts and non-uniform in regard to the conclusions drawn by the experts. Therefore, a need in the art exists for improved solutions for evaluating objects that are more efficient and uniform in their conclusions than the conventional schemes described above.

SUMMARY

The above-described problems are addressed and a technical solution is achieved in the art by systems and methods for evaluating object condition, according various embodiments of the present invention.

In some embodiments of the present invention, a method for evaluating an object is provided. The method is implemented at least in part by a data processing device system. The method includes receiving input. The input includes indications of a plurality of flaws present on or in the object, a flaw type for each of the flaws, and a severity for each of the flaws. The method also includes determining weighting factors associated with the plurality of flaws, the weighting factors dependent at least on the severities of the flaws. In addition, the method includes determining a quality-score indicating a condition of the object based at least on at least some of the weighting factors and the flaw types for at least some of the flaws. Further, the method includes storing the quality-score in a processor accessible memory device system.

In some embodiments, the method also includes determining a plurality of intermediate quality scores. One of the intermediate quality scores can indicate a preliminary assessment of the condition of the object, and the quality score can be determined based at least on at least some of the weighting factors, the flaw types for at least some of the flaws, and the intermediate quality scores.

In some embodiments, a first of the intermediate quality scores is determined based at least on an assessment of damage to the object due to flaws having a particular flaw type. The particular flaw type is one of the flaw types that presents the most damage to the object as compared to the others of the flaw types. A second of the intermediate quality scores can be determined based at least on the first of the intermediate quality scores and a flaw type determined to present the next-most damage to the object after the particular flaw type.

In some embodiments, the number of intermediate quality scores is inversely proportional to object quality.

In some embodiments, the severity of at least some of the flaws indicates at least a flaw location of the corresponding flaw, and the weighting factors of the corresponding flaws each are dependent at least on the corresponding flaw location.

In some embodiments, the severity of at least some of the flaws indicates at least a flaw size of the corresponding flaw, and the weighting factors associated with the corresponding flaws each are dependent at least on the corresponding flaw size.

In some embodiments, the severity of at least some of the flaws indicates at least a severity type of the corresponding flaw, the severity type being different from the flaw type. In some of these embodiments, the severity of at least some of the flaws that indicates a severity type also indicates at least a flaw size of the corresponding flaw of the corresponding severity type, and the weighting factors associated with the corresponding flaws each are dependent at least on the corresponding combination of severity type and flaw size. Also in some of these embodiments, the severity of at least some of the flaws that indicates a severity type also indicates at least a flaw location of the corresponding flaw of the corresponding severity type, and the weighting factors associated with the corresponding flaws each are dependent at least on the corresponding combination of severity type and flaw location. The severity of at least some of the flaws that indicates a severity type and a flaw size can also indicate at least a flaw location of the corresponding flaw, and the weighting factors associated with the corresponding flaws can each be dependent at least on the corresponding combination of severity type, flaw size, and flaw location.

In some embodiments, the method also includes generating a report identifying at least all of the flaws and their corresponding weighting factors, flaw types, and severities; and storing the report in the processor-accessible memory-device system. In some embodiments, the method further includes associating the quality score with a word-based score; and storing the word-based score in the processor-accessible memory-device system.

In some embodiments, the flaw types are selected from a set of available flaw types stored in a database, and in this case, the method can additionally include receiving second input including an indication that an existing one of the available flaw types should be changed or a new available flaw type should be added to the set of available flaw types; and changing the existing one of the available flaw types in the database or adding the new available flaw type to the database in accordance with and in response to receiving the second input.

In some embodiments, the determining of the weighting factors includes retrieving the weighting factors from a database. In this case, the method can further include receiving second input including an indication that a particular one of the weighting factors in the database should be changed; and changing the particular one of the weighting factors in accordance with and in response to receiving the second input.

In some embodiments, the flaw locations are selected from a set of available flaw locations stored in a database. In these embodiments, the method can also include receiving second input including an indication that an existing one of the available flaw locations should be changed or a new available flaw location should be added to the set of available flaw locations; and changing the existing one of the available flaw locations in the database or adding the new available flaw location to the database in accordance with and in response to receiving the second input.

In some embodiments, the flaw sizes are selected from a set of available flaw sizes stored in a database. In these embodiments, the method can also include receiving second input including an indication that an existing one of the available flaw sizes should be changed or a new available flaw size should be added to the set of available flaw sizes; and changing the existing one of the available flaw sizes in the database or adding the new available flaw size to the database in accordance with and in response to receiving the second input.

In some embodiments, the severity types are selected from a set of available severity types stored in a database. In this situation, the method can additionally include receiving second input including an indication that an existing one of the available severity types should be changed or a new available severity type should be added to the set of available severity types; and changing the existing one of the available severity types in the database or adding the new available severity type to the database in accordance with and in response to receiving the second input.

In some embodiments, the determining of the plurality of intermediate quality scores includes determining the intermediate quality scores based upon discount factors stored in a database. In some of these embodiments, the method further includes receiving second input including an indication that one of the discount factors should be changed; and changing the one of the discount factors in the database in accordance with and in response to receiving the second input.

In some embodiments, the above-described methods can be implemented by a data processing device system executing instructions stored on a processor-accessible memory device system. The instructions, when executed by the data processing device system, cause the data processing device system to implement the above-described methods.

In some embodiments, the above-described methods are implemented by a system including a data processing device system; and a processor-accessible memory device system communicatively connected to the data processing device system. In some of these embodiments, the processor-accessible memory device system stores instructions that, when executed by the data processing device system, causes the data processing device system to implement the above described methods.

In addition to the embodiments described above, further embodiments will become apparent by reference to the drawings and by study of the following detailed description.

BRIEF DESCRIPTION OF THE DRAWINGS

The present invention will be more readily understood from the detailed description of preferred embodiments presented below considered in conjunction with the attached drawings, of which:

FIG. 5 illustrates an example of a weighting factor database that can be referenced in step 204 to determine weighting factors, according to embodiments of the present invention;

FIG. 6 illustrates an example calculation that can facilitate a determination of an intermediate quality score in step 206 in FIG. 2 or FIG. 3, according to embodiments of the present invention;

FIG. 7 illustrates a grading matrix that can be referenced in step 206 in FIG. 2 or FIG. 3, according to embodiments of the present invention.

Figure 1:
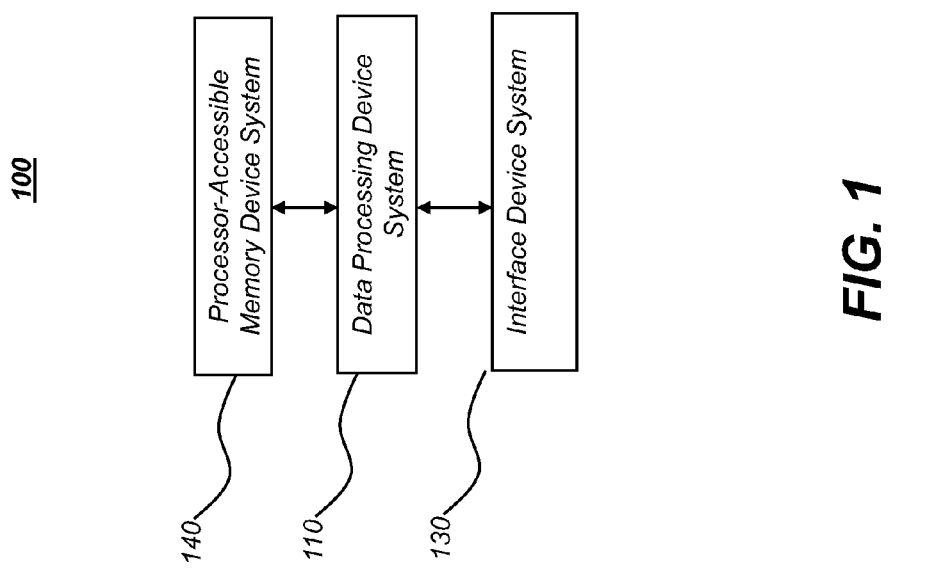
FIG. 1 illustrates a system for evaluating a condition of an object, according to embodiments of the present invention.

It is to be understood that the attached drawings are for purposes of illustrating the concepts of the invention and may not be to scale.

DETAILED DESCRIPTION

Embodiments of the present invention provide systems and methods for evaluating a condition of an object, such as a physical object, with improved uniformity as compared to conventional schemes. For example, embodiments of the present invention predefine flaw types and flaw severities associated with flaws that may potentially be present in a certain category of objects. Such information is predefined in a data processing device system along with rules for evaluating the condition of objects of the certain category based at least on the predefined flaw types and severities. ("Predefined" in this context, means defined prior to the inputting or describing of flaws in or on an object to the data processing device system by the user, e.g., prior to step 202 in FIG. 2, described below.) In this manner, any user, expert or not, can evaluate the condition of an object merely by identifying to the data processing device system the flaws that are present in the object according to the predefined flaw types and severities. Accordingly, uniform evaluation results can be obtained, and can be obtained promptly without waiting for an expert to manually evaluate the object and with less expense.

Further, in some embodiments of the present invention, the predefined flaw types, predefined severities, and predefined rules can be changed by a user or otherwise at any time, thereby making the evaluation process fully configurable. An audit trail or history of these changes can be retained by the data processing device system to facilitate more educated changes in the future. Version control and access rights can be implemented to safeguard against unauthorized or inappropriate changes.

Also in some embodiments, a different set of predefined flaw types, severities, and rules can be generated for each of a plurality of different categories of objects. For example, a first set of flaw types, severities, and rules can be defined by a user or otherwise, for evaluating movie posters or other ephemera. A second set of flaw types, severities, and rules can be defined by a user or otherwise, for evaluating diamonds. Accordingly, embodiments of the present invention provide object evaluation systems and methods that can evaluate the condition of any object. Therefore, one of ordinary skill in the art will appreciate that the present invention is not limited to any particular type of object.

The invention is inclusive of combinations of the embodiments described herein. References to a particular embodiment and the like refer to features that are present in at least one embodiment of the invention. Separate references to an embodiment or particular embodiments or the like do not necessarily refer to the same embodiment or embodiments; however, such embodiments are not mutually exclusive, unless so indicated or as are readily apparent to one of skill in the art. The use of singular, plural, or both singular and plural when referring to a method or methods, system or systems, and the like is not limiting. It should be noted that, unless otherwise explicitly noted or required by context, the word "or" is used in this disclosure in a non-exclusive sense.

FIG. 1 illustrates a system 100 for evaluating an object, according to embodiments of the present invention. The system 100 includes a data processing device system 110, an interface device system 130, and a processor-accessible memory device system 140. The processor-accessible memory device system 140 and the interface device system 130 are communicatively connected to the data processing device system 110.

Figure 2:
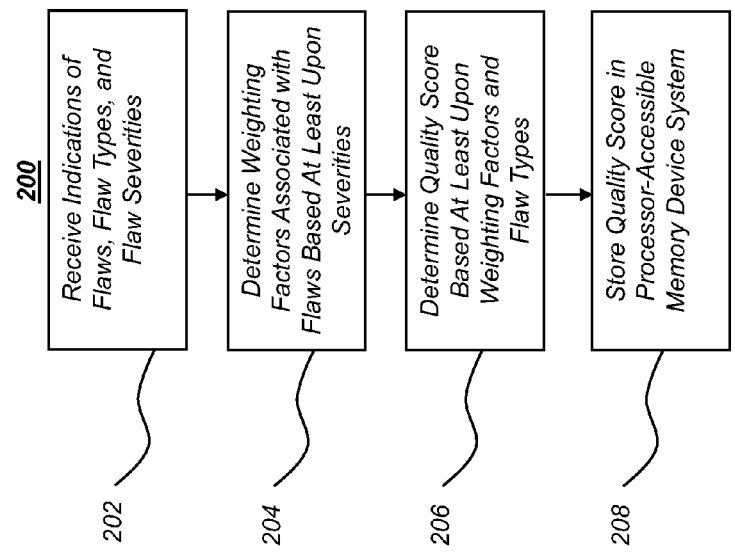
FIG. 2 illustrates a method for evaluating a condition of an object, according to embodiments of the present invention.
Figure 3:
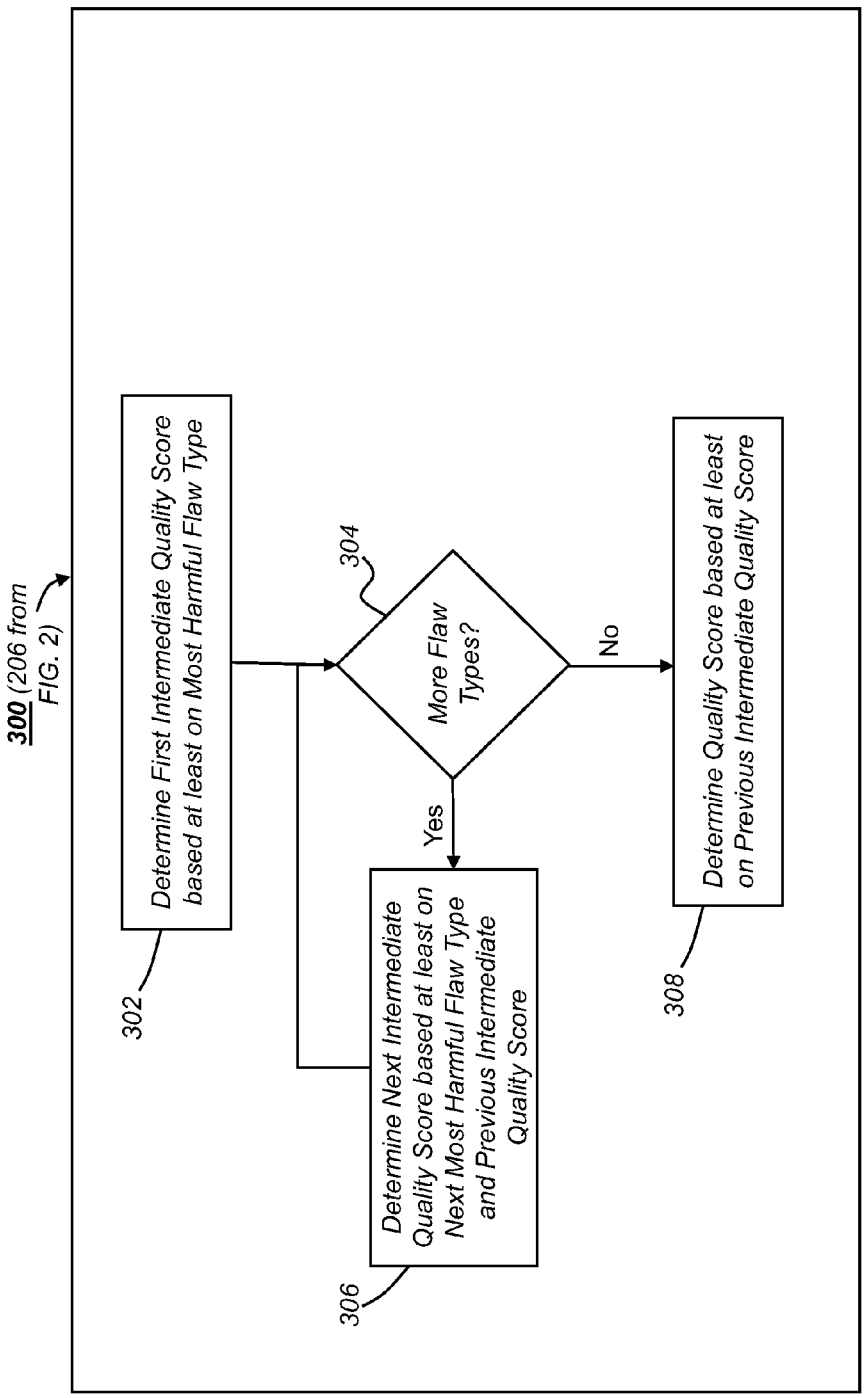
FIG. 3 illustrates an exploded view of step 206 of determining a quality score illustrated in the method of FIG. 2, according to embodiments of the present invention.

The data processing device system 110 includes one or more data processing devices that are configured to implement the processes of the various embodiments of the present invention, including the example processes of FIGS. 2 and 3 described herein. The phrases "data processing device" and "data processor" each are intended to include any data processing device, such as a central processing unit ("CPU"), a desktop computer, a laptop computer, a mainframe computer, a personal digital assistant, a Blackberry™, cellular phone, or any other device for processing data, managing data, or handling data, whether implemented with electrical, magnetic, optical, biological components, or otherwise.

The processor-accessible memory device system 140 includes one or more processor-accessible memory devices configured to store information, including the information needed to execute the processes of the various embodiments of the present invention, including the example information shown in FIGS. 4-7 that can be used by the data processing device system 110 to execute the example processes of FIGS. 2 and 3 described herein. Because the system 140 is a device system, it does not include transitory propagating signals per se, and is, by definition, non-transitory. The processor-accessible memory device system 140 can be a distributed processor-accessible memory device system including multiple processor-accessible memory devices communicatively connected to the data processing device system 110 via a plurality of computers and/or devices. On the other hand, the processor-accessible memory device system 140 need not be a distributed processor-accessible memory device system and, consequently, can include one or more processor-accessible memories located within a single data processor or device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs.

The phrase "communicatively connected" is intended to include any type of connection, whether wired or wireless, between devices, data processors, or programs in which data can be communicated. Further, the phrase "communicatively connected" is intended to include a connection between devices or programs within a single data processor, a connection between devices or programs located in different data processors, and a connection between devices not located in data processors at all. In this regard, although the processor-accessible memory device system 140 is shown separately from the data processing device system 110, one of ordinary skill in the art will appreciate that the processor-accessible memory device system 140 can be located completely or partially within the data processing device system 110. Further in this regard, although the interface device system 130 is shown separately from the data processing device system 110, one of ordinary skill in the art will appreciate that such system can be located completely or partially within the data processing device system 110.

The interface device system 130 can include a mouse, a keyboard, another computer, network interface circuitry, a processor-accessible memory, or any device or combination of devices from which data is input to the data processing device system 110. The interface device system 130 also can include a display device, a processor-accessible memory, network interface circuitry, or any device or combination of devices to which data is output by the data processing device system 110. In this regard, if the interface device system 130 includes a processor-accessible memory, such memory can be part of the processor-accessible memory device system 140 even though the interface device system 130 and the processor-accessible memory device system 140 are shown separately in FIG. 1.

FIG. 2 illustrates a method 200 for evaluating an object that is implemented by the system 100 shown in FIG. 1, according to embodiments of the present invention. In a step 202, the data processing device system 110 receives, as input from the interface device system 130, indications of at least a plurality of flaws present on or in an object, a flaw type for each of the flaws, and a severity for each of the flaws.

Figure 4:
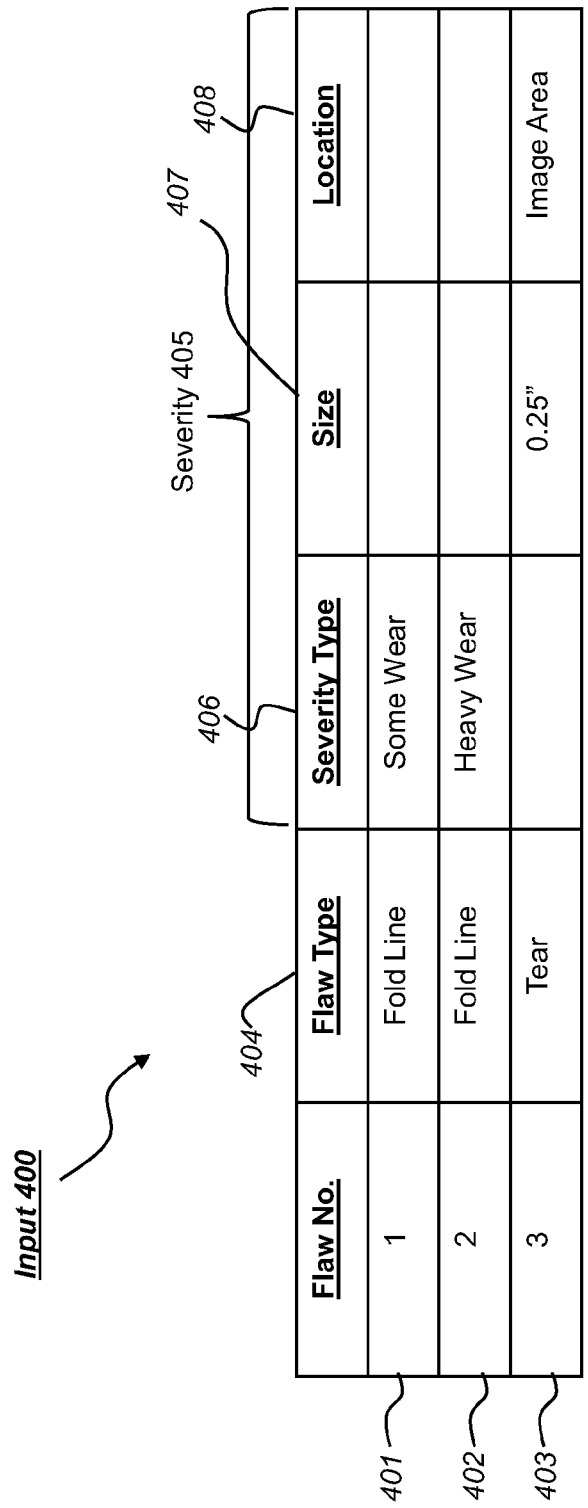
FIG. 4 illustrates an example of input that can be received in step 202 illustrated in the method of FIG. 2, according to embodiments of the present invention.

FIG. 4 illustrates an example of input 400 that can be received in step 202, according to embodiments of the present invention. In this example, the input includes indications of a plurality of flaws 401-403 (respectively identified as flaw numbers 1-3), a flaw type 404 for each of the flaws 401-403, and a severity 405 associated with each of the flaws 401-403. The severity 405 of a particular flaw is indicated in these embodiments by a severity type 406, a size 407, a location 408, or combinations thereof, of the particular flaw. In the example of FIG. 4, flaw 401 has a flaw type 404 of "Fold Line" and a severity type 406 indicating that this "Fold Line" flaw has "Some Wear". Flaw 402 also has a flaw type 404 of "Fold Line", but has a severity type 406 indicating that this particular "Fold Line" flaw has "Heavy Wear". Flaw 403 has a flaw type 404 of "Tear" and a severity 405 indicating that this particular "Tear" flaw has a size 407 of 0.25 inches and has a location 408 in an image area of the object, which could be a movie poster having an image area and a border area. As shown in FIG. 4, not all of the sub-categories 406-408 of severity 405 need to be identified.

In some embodiments of the present invention, the input 400 is input via a graphical user-interface presented to a user via a display in the interface device system 130 in FIG. 1. For example, the user can be prompted by the data processing device system 110 to input a first flaw 401 and then select a flaw type 404 for the flaw 401 from a drop-down list known in the art that identifies all available flaw types that have been predefined in the system 100. When the flaw type 404 is selected from the drop-down list, the user can be prompted to select a value for one or more of the particular sub-categories 406-408 of severity 405 that are available for the selected flaw type 404.

In this case, the selected flaw type 404 for flaw 401 is "Fold Line". Assume for illustrative purposes that only the severity type sub-category 406 is available for "Fold Line" flaw types 404 as an option for specifying severity. Consequently, the user can be prompted with a drop-down list identifying all available severity types 406 associated with "Fold Line" flaw types. Assume, for example, that the available severity types 404 for fold lines are "Some Wear", "Heavy Wear", and "Separation". In this case, the user selects "Some Wear" for the severity type 406 for flaw 401. The information for flaws 402 and 403 can be input in a similar manner. However, the present invention is not limited to the manner in which the input 400 is provided to and received by the data processing device system 110 in step 202 in FIG. 2, and any technique for inputting data, either from a user or otherwise, can be used. For example, the information provided at step 202 in FIG. 2 can be provided in an automated manner by an image-acquisition device, such as a digital camera, acquiring an image or images of the object, and then the data processing device system 110 can analyze the image or images of the object to identify the flaws, flaw types, severity types, size, and location, using image processing techniques known in the art. In this regard, it should be noted that the data received at step 202 by the data processing device system 110 represents the physical, tangible object being evaluated, and this data is operated on and transformed by the data processing device system 110 at later steps, described below, into a different state or thing, such as the condition of the object being evaluated or a report or a certificate indicating the condition of the object being evaluated. In addition, although FIG. 4 and several of the other figures discussed below illustrate particular flaw types and severity information, such as severity type, size, and location, the present invention is not limited to any particular flaw types and severity information.

In step 204 in FIG. 2, the data processing device system 110 determines weighting factors associated with at least some of the flaws indicated by the input received in step 202. These weighting factors are dependent at least on the severities associated with the corresponding flaws, the severities having been indicated by the input received in step 202.

For example, FIG. 5 illustrates a weighting factor database 500 stored in the processor-accessible memory device system 140, according to embodiments of the present invention. Table I, at the end of this detailed description, illustrates an example of a more complete version of the weighting factor database 500. However, the invention is not limited to any particular form or content of a weighting factor database, and FIG. 5 and Table I are provided for illustration purposes only.

In some embodiments, the data processing device system 110 accesses the database 500 of FIG. 5 in step 204 to determine the weighting factors for each of the flaws 401-403 indicated by input 400. The weighting factor database 500 is shown as a table in FIG. 5. However, any manner of representing and organizing data can be used. The same applies for the tables of FIGS. 4, 6, and 7.

In some embodiments, the weighting factor database 500 defines a weighting factor 501 for each possible combination of flaw type 502 and severity 506 predefined in the system 100. For purposes of clarity, however, the database 500 in FIG. 5 illustrates only a subset of these possible combinations. In particular, the database 500 lists flaw types 502 of "Fold Line" and "Tear". For each "Fold Line" flaw type, the possible severity types 503 are "Some Wear", "Heavy Wear", and "Separation". For "Fold Line" flaw types 502 that have a severity type 503 of "Some Wear" or "Heavy Wear", the severity 506 of such flaws is indicated only by the severity type 503, and, in this regard, the severity 506 is not indicated by a size 504 or a location 505. For "Fold Line" flaw types 502 having a severity type 503 of "Separation", the severity 506 also is indicated by a size 504 of the corresponding separations. Although any number of sizes 504 can be listed in this regard, the database 500 only illustrates separation size options of 0.25 inches and 0.5 inches for purposes of clarity.

For "Tear" flaw types 502, the severity 506 is indicated by a size 504 and a location 505 of the corresponding flaw, and is not indicated by a severity type 503. Two types of locations 505 are possible in the example of FIG. 5: a tear in the "Border Area" of an object, such as a movie poster, or a tear in the "Image Area" of an object. For each location 505 ("Border Area" and "Image Area"), any number of sizes 504 of the tear can be specified. In the example database 500, only sizes 504 of 0.25 inches and 0.5 inches are illustrated for each location 505 ("Border Area" and "Image Area") for purposes of clarity.

Accordingly, each row of the database 500 represents a unique combination of flaw type 502 and severity 506 as compared to every other row in the database 500. And for each row, a weighting factor 501 is provided. In the example of FIG. 5, it can be seen that a fold line exhibiting heavy wear has a greater weighting factor than a fold line exhibiting some wear, and that a fold line exhibiting a separation of 0.5 inches has a greater weighting factor than a fold line exhibiting a smaller separation of 0.25 inches. (A fold line separation is caused by a fold line wearing through a poster, for example, but typically is clean.) Similarly, a longer tear has a greater weighting factor than a shorter tear, when located within the same area (border or image). However, a tear in an image area of the object (e.g., a movie poster) has a greater weighting factor than an equivalently sized tear in the border area. (A tear does not have a fold associated therewith, like a fold line).

Accordingly, it can be seen that the weighting factors in these embodiments are proportional to the severity of damage to the object and, consequently, are inversely proportional to the quality or value of the condition of the object. One of ordinary skill in the art will appreciate, however, that the invention is not limited in this regard, and any manner of indicating relative damage to the condition of an object amongst possible flaw types and severities can be used. For example, the weighting factors 501 could instead be inversely proportional to the severity of damage to the object.

Also, it should be noted that the present invention is not limited to any particular condition of an object being evaluated. The condition being evaluated can be, for example, an overall condition of an object or a condition of a portion of an object. In addition, although integers are illustrated as weighting factors 501, any type of number can be used. Further, although FIG. 5 illustrates an example set of possible combinations of flaw types 502 and severities 506, the invention is not limited to any particular flaw types, severities, and combinations thereof.

In order to determine the weighting factor 501 in step 202 for each flaw 401-403 indicated by input 400, the data processing device system 110 can query the database 500 with each flaw 401-403, and the database 500 can return the corresponding weighting factors 501 to the data processing device system 110. The data processing device system 110 can then assemble, for example, the data illustrated by FIG. 6. It can be seen from FIG. 6 that flaw 401 is determined to have a weighting factor of 20, flaw 402 is determined to have a weighting factor of 200, and flaw 403 is determined to have a weighting factor of 15.

In step 206 in FIG. 2, the data processing device system 110 determines a quality score indicating a condition of an object based at least on the weighting factors determined in step 204 and the flaw types of at least some of the flaws indicated by the input received in step 202. FIG. 3 illustrates an exploded view 300 of one possible implementation of step 206, according to embodiments of the present invention. In the embodiments of FIG. 3, the quality score ultimately determined at the conclusion of step 206 can be determined based on one or more intermediate quality scores that are calculated first. The intermediate quality scores can indicate a preliminary assessment of a condition of an object and can be determined based at least on an assessment of damage, e.g., total damage, to the object or a portion of the object due to flaws having a particular flaw type.

For example, in step 302, the data processing device system 110 determines a first intermediate quality score based at least on an assessment of damage to an object due to flaws of a particular flaw type. The particular flaw type is one of the flaw types indicated by the input 400 that presents the most damage to the object as compared to the other flaw types. By "most damage", it is meant that the condition or value of the object or portion thereof is most harmed.

Returning to the example of FIG. 6, the flaws 401-403, which were input in step 202, include two flaw types: "Fold Line" and "Tear". The damage to the object due to flaws of each of these flaw types can be assessed by the data processing device system 110 as part of step 302 in at least two parts: (1) by summing the weighting factors of the flaws of each flaw type, and (2) preliminarily evaluating the condition of the object for each flaw type based at least on the respective cumulative weighting factors from part (1).

Regarding part (1), for example, flaws 401 and 402 both belong to the flaw type "Fold Line" and, therefore, their weighting factors are summed. In this case, the cumulative weighting factor for flaws of the "Fold Line" flaw type is 220. Since only one flaw 403 belongs to the "Tear" flaw type, the cumulative weighting factor for the "Tear" flaw type is 15, which is the weighting factor of flaw 403.

Regarding part (2), the data processing device system 110 preliminarily evaluates the condition of the object independently for each flaw type, as if the object only had flaws of the flaw type presently being used to evaluate the object. To elaborate, FIG. 7 illustrates an example of a grading matrix 700 that can be referenced at least to preliminarily evaluate the condition of an object or a portion thereof. Tables II(A)-(C), at the end of this detailed description, illustrate an example of a more complete version of the grading matrix 700. However, the invention is not limited to any particular form or content of a grading matrix, and FIG. 7 and Tables II(A)-(C) are provided for illustration purposes only.

The matrix 700 includes a sequence of grades 701, which respectively are quality scores indicating a condition of an object. Grade names 702 are word-based scores associated, respectively, with each of the grades 701. Column 703 indicates the maximum cumulative weighting factor per grade 701 for flaws having the "Fold Line" flaw type. Column 704 indicates the maximum cumulative weighting factor per grade 701 for flaws having the "Tear" flaw type.

Working from the example in FIG. 6, the "Fold Line" flaw type has a cumulative weighting factor of 220, which exceeds the maximum weighting factor of 200 for a "Very Fine" grade of 8.5, but is less than the maximum weighting factor of 300 for a "Very Fine-" grade of 8.0. Accordingly, the data processing device system 110 preliminarily evaluates the condition of the object as 8.0 as part of step 302 under the assumption that the object only had flaws of the "Fold Line" flaw type.

The "Tear" flaw type, on the other hand, has a cumulative weighting factor of 15, which results in a grade of 9.0, assuming the object only had flaws of the "Tear" flaw type.

With this information, the data processing device system 110 determines that the "Fold Line" flaw type presents the most damage to the object, because this flaw type independently results in the lowest grade (indicating the condition of the object), as compared to the other flaw types.

A review of the example grading matrix 700 in FIG. 7 reveals that the maximum cumulative weighting factors between columns 703 and 704 need not be the same for the same grade. For example, a grade of 9.0 for the "Fold Line" flaw type can be obtained with a corresponding cumulative weighting factor between 21 and 120 inclusive. However, a grade of 9.0 for the "Tear" flaw type can be obtained with a corresponding cumulative weighting factor between 11 and 30 inclusive. Allowing these relative differences in cumulative weighting factors between flaw types facilitates ease of design, because it allows a developer to determine a grading system for each flaw type relatively independently of the other flaw types, as compared to requiring the cumulative weighting factors to result in the same scores across all flaw types.

Having identified the most damaging flaw type, the data processing device system 110, in some embodiments, calculates the first intermediate quality score in step 302 based at least on the grade associated with the most damaging flaw type. In this case, the grade associated with the "Fold Line" flaw type is 8.0. In some embodiments, the first intermediate quality score $IQS_1$ is determined according to the following equation (1):

$$IQS_1 = +10 - ((10 - G_1) * D_1) \qquad (1)$$

The "+10" in equation (1) represents, for example, the maximum possible value for a grade indicating the condition of the object, and the minus after the "+10" indicates that the presence of flaws will reduce the intermediate quality score from the maximum value. "$G_1$" represents the grade associated with the most harmful flaw type, which in this case, is the grade 8.0 associated with the "Fold Line" flaw type as shown in FIG. 7. "$D_1$" represents a flaw discount factor associated with the most harmful flaw type. According to some embodiments, $D_1$ is 0.8. Accordingly, the first intermediate quality score using the examples of FIGS. 6 and 7 is calculated as follows:

$$IQS_1 = +10 - ((10 - 8.0) 0.8) = 8.4$$

As can be seen, the first intermediate quality score is 8.4, which is higher than the grade of 8.0 assigned to the "Fold Line" flaw type in FIG. 7. This boosting of the grade indicates that a quality score should improve if the corresponding object has or substantially has flaws of only a single flaw type. As will become clearer below, pursuant to some embodiments, if the object at issue has flaws of only a single flaw type, its final quality score determined in step 308 will be the first intermediate quality score determined in step 302. In this example, the final quality score would be 8.4, which is greater than the grade of 8.0 originally assigned to the object due to the "Fold Line" flaws in FIG. 7. Accordingly, a premium can be placed on objects having or substantially having flaws of only a single flaw type.

Having determined the first intermediate quality score in step 302, it is next determined in step 304 whether more flaw types exist for the object that have not been factored into the previously determined intermediate quality score. Continuing with the example of FIGS. 6 and 7, the first intermediate quality score represents only the damage caused by the "Fold Line" flaw type. Damage caused by the "Tear" flaw type is not reflected in the first intermediate quality score. Accordingly, a determination of "yes" is made in step 304.

With a determination of "yes" in step 304, processing proceeds to step 306, where a next intermediate quality score is determined based at least on the next most harmful flaw type and the previously determined intermediate quality score. Continuing with the example of FIGS. 6 and 7, the next most harmful flaw type is the "Tear" flaw type. Aside from being the only other flaw type in this example, the "Tear" flaw type is the next most harmful, because the flaw 403 associated with this flaw type would have caused the object to be assigned a grade of 9.0 (FIG. 7, assuming only tear flaws were present in the object), which is the second lowest grade of the two flaw types ("Fold Line" and "Tear") present in the object.

Having identified the next most harmful flaw type, the data processing device system 110 determines the next intermediate quality score in step 306. According to some embodiments of the present invention, the next intermediate quality score $IQS_N$ is calculated using the following equation (2):

$$IQS_N = (P) - ((10 - G_N) * D_N) \qquad (2)$$

"P" represents the previous intermediate quality score, which in the present example, is 8.4, the value of the first intermediate quality score. "$G_N$" represents the grade associated with the cumulative weighting factor of the present flaw type (e.g., FIG. 7), which was determined as the next most harmful flaw type. Continuing with the example of FIGS. 6 and 7, the present flaw type is the "Tear" flaw type and, therefore, $G_N$ is 9.0. "$D_N$" represents a flaw discount factor associated with the present flaw type. According to some embodiments, "$D_N$" is 0.1 for the second most harmful flaw type. With "P" equal to 8.4, "$G_N$"=9.0, and "$D_N$" equal to 0.1, the second intermediate quality score is calculated as follows:

$$IQS_N = 8.4 - ((10 - 9.0) 0.1) = 8.3$$

It can be seen that the second intermediate quality score is less than the first intermediate quality score, because more flaws are present and accounted for in this evaluation of the object. Accordingly, each subsequently calculated intermediate quality score generally is lower than the previously calculated intermediate quality score, and, therefore, the number of intermediate quality scores generally is inversely proportional to object quality. However, as the flaw types associated with subsequently calculated intermediate quality scores become associated with more minor flaws, the intermediate quality scores tend to flatten out. For instance, the 0.25" tear in the image area associated with flaw 403 is deemed minor in nature, and, therefore, the decrease between the first and second intermediate quality scores in this example is small. This example also illustrates a case where an object can have two flaw types and still have a quality score greater than the initial grade associated with the most harmful flaw type (e.g., the "Fold Line" flaw type in FIG. 7 having an initial grade of 8.0). Accordingly, so long as the second and subsequently most harmful flaw types are minor enough in nature, a boost to the initial grade associated with the most harmful flaw type can still be provided.

Having calculated the second intermediate quality score in step 306, processing returns to step 304 to determine whether more flaw types exist that have not been factored into the previously determined intermediate quality score. If more of such flaw types exist, processing returns to step 306 where the next intermediate quality score is calculated, for example, based on equation (2), above, for the next most harmful flaw type. In some embodiments, the factor "$D_N$" is 0.1 for every subsequently calculated intermediate quality score. However, "$D_N$" can have any other value depending upon design choice.

In some embodiments, a maximum number of intermediate quality scores can be set, so that step 304 not only determines whether other flaw types have yet to be considered, but also determines whether such maximum number of intermediate quality scores has been reached. In some embodiments, the maximum number of intermediate quality scores is five. However, this number can be set to any number depending on design choice. In these embodiments, even if more flaw types exist in step 304, processing would proceed to step 308 if the maximum number of intermediate quality scores has been reached. Consequently, processing time and resources can be saved by truncating the intermediate score calculations when the severity of the remaining flaw types becomes so minor that the final quality score would not be substantially impacted by the flaws associated with such flaw types.

Continuing with the examples of FIGS. 6 and 7, it is determined in step 304 that no more flaw types exist, because both the "Fold Line" flaw type and the "Tear" flaw type have been factored into the previous intermediate quality score. Accordingly, processing proceeds to step 308.

In step 308, the data processing device system determines a final quality score indicating a condition of the object based at least on the previous intermediate quality score. It should be noted that the previous intermediate quality score was determined based on the weighting factors and flaw types shown in FIGS. 6 and 7 and associated with flaws 401-403. Consequently, it can be said that the final quality score determined in step 308 is calculated based at least on the weighting factors and flaw types of the flaws 401-403.

In some embodiments, the final quality score is determined in step 308 by directly assigning the previous intermediate quality score as the final quality score, or by applying rounding processing to the previous intermediate quality score to arrive at the final quality score. In embodiments that use rounding processing, an intermediate quality score ending in a 0.1 or a 0.2 is rounded to the lower whole number (e.g., 8.2 rounded to 8.0), an intermediate quality score ending in a 0.3 or a 0.4 is rounded to the higher half number (e.g., 8.3 rounded to 8.5), an intermediate quality score ending in a 0.6 or a 0.7 is rounded to the lower half number (e.g., 8.6 is rounded to 8.5), and an intermediate quality score ending in a 0.8 or a 0.9 is rounded to the higher whole number (e.g., 8.8 is rounded to 9.0). Using this technique while continuing the example of FIGS. 6 and 7, the second intermediate quality score of 8.3 results in a determination of a final quality score of 8.5 ("Very Fine") in step 308. This final quality score is stored in the processor-accessible memory device system 140 in step 208 in FIG. 2. Although the phrase "final quality score" is used herein when describing step 308, such quality score need not actually be final and can be subjected to further processing subsequent to step 308.

As discussed above, some embodiments of the present invention predefine flaw types and flaw severities associated with flaws that may potentially be present in a certain category of objects. For example, the flaw types 502 in FIG. 5 and the severities 506 in FIG. 5 can be predefined, and the data processing device system 110 can be configured to prompt a user to select from these predefined flaw types and severities when entering input in step 202 in FIG. 2.

In addition, the data processing device system 110 can be configured to receive input via the user interface device system 130, and based on this input, modify or newly generate flaw types (e.g., 502 in FIG. 5), severities (e.g., 506 in FIG. 5, including severity type (e.g., 503 in FIG. 5), size (e.g., 504 in FIG. 5), and location (e.g., 505 in FIG. 5)), or both flaw types and severities. Further in this regard, the data processing device system 110 can be configured to receive input via the user interface device system 130, and based on this input, modify or newly generate rules by which the data processing device system 110 interacts with the flaw types and severities of flaws to evaluate the condition of an object, according to various embodiments of the present invention. Examples of such rules include (a) grading matrices (e.g., 700 in FIG. 7), (b) weighting factors (e.g., 501 in FIG. 5), (c) maximum number of intermediate quality scores calculated, for example, in step 304 in some embodiments, (d) discount factors (e.g., $D_1$, $D_N$ in equations (1) and (2), respectively), (e) equations (e.g., equations (1) and (2)) that are dependent upon grading matrices, weighting factors, discount factors, or other information that facilitates the evaluation of the condition of an object, or (e) combinations of the aforementioned grading matrices, weighting factors, maximum number of intermediate quality scores calculated, discount factors, and equations.

Also as discussed above, a different set of predefined flaw types, predefined severities, and predefined rules can be generated for each of a plurality of different categories of objects. The present invention is not limited to any particular category of object, and one of ordinary skill in the art will appreciate that the grading matrices, factors, equations, or variations thereof can be adapted to evaluate any object, whether man-made or naturally occurring. In this regard, a user could be prompted, for example, before step 202 in FIG. 2, to identify to the data processing device system 110, a category of object being evaluated. With a category of object identified, the data processing device system 110 can select the proper set of flaw types, severities, and rules associated with the selected category of object.

In addition, having stored a quality score in step 208 in the processor accessible memory device system 140, the data processing device system 110 can also be configured to output the "final quality score" via some other device besides or in addition to a memory device system included in the interface device system 130. For instance, the "final quality score" could be output on a display device, or via a printer device, under the control of the data processing device system 110 for viewing by a user. Or, if image(s) of the object being evaluated were acquired at step 202 in FIG. 2 in order for the data processing device system 110 to identify the flaws in the object, for example, the image(s) of the object could be output via any device in the interface device system 130 in a manner that highlights the identified flaws and shows the "final quality score" indicating the condition of the object in view of the identified flaws. In this regard, the data processing device system 110 can be configured to generate a report or certificate indicating the quality score, all of the flaws, their flaw types, their severities, their weighting factors, or combinations thereof, associated with the object that was evaluated. Such a report or certificate on the condition of the object can not only show the flaws on the object in an accentuated (e.g., highlighted) manner by displaying one or more acquired images of the object and the "final quality score", but also reveal in a systematic sequence the manner in which the "final quality score" was calculated, as described above, for example, with respect to steps 204 and 206 in FIG. 2, and the whole of FIG. 3. Such a report or certificate can be stored in the processor accessible memory device system 140.

Figure 8:
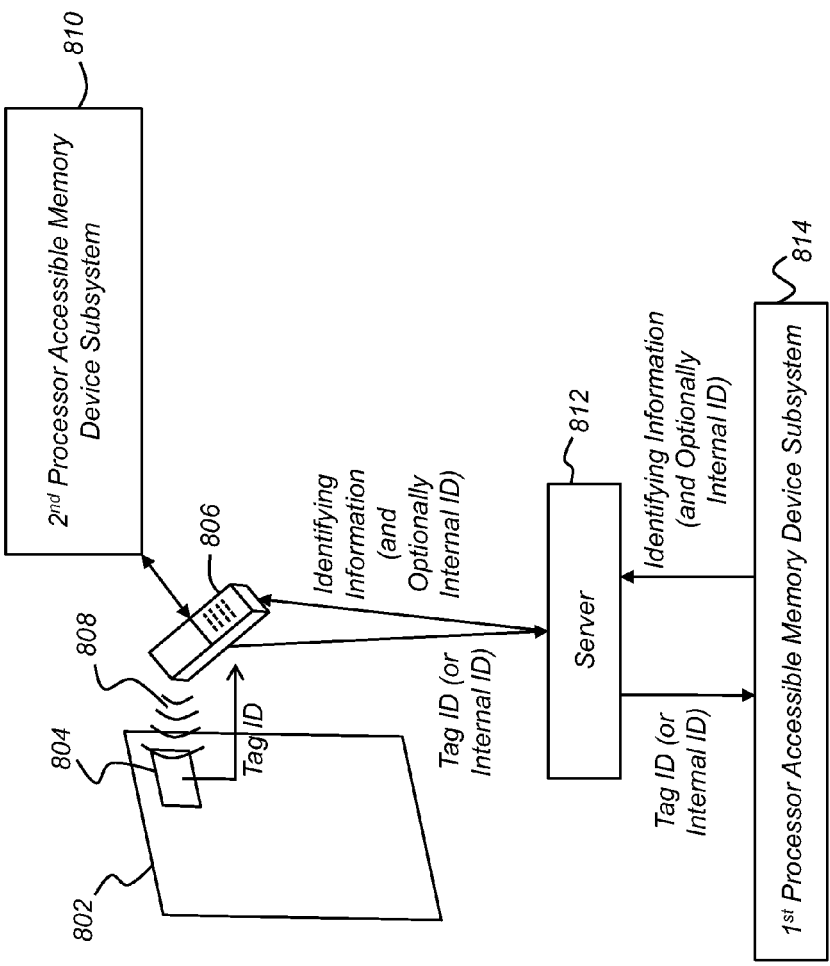
FIG. 8 illustrates a system for ensuring object authenticity, according to some embodiments of the present invention.

Further, it can be advantageous to implement the above-discussed evaluation of object condition in a particular system, such as that shown in FIG. 8, which can be a specific implementation of the system 100 shown in FIG. 1, according to some embodiments of the present invention. The system 800 shown in FIG. 8 is disclosed and described in co-pending U.S. patent application Ser. No. 12/914,451, by Spoor, et al., filed concurrently with the present application, having a title of, "IDENTIFYING AND ENSURING THE AUTHENTICITY OF OBJECTS", which is not known in the art, and is hereby incorporated herein by reference.

In this regard, it can be advantageous, when evaluating object condition according to any of the various embodiments described herein, to store the "final quality score" at step 208 along with an identifier associated with a tag 804 and any other information identifying the object 802 being evaluated, such as one or more images of the object 802. The tag 804 can be attached to the object 802 being evaluated or can be attached to a report or certificate associated with the object 802. When the identity of the object 802 needs to be verified, a hand-held tag-reading device 806 or other tag reading device known in the art, can be used to retrieve the tag identifier, for example, by bombarding a radiation reflective tag 804 with appropriate radiation 808. (However, a radiation-reflective tag need not be used, and any tag capable of providing a tag identifier to a reading device can be used. An example of a hand-held reading device 806 is the CS101-2 Handheld Reader, known in the art, from Convergence Systems Limited having a headquarters in Hong Kong.) The tag identifier or some other identifier (e.g., an "internal identifier") associated with the tag identifier can be used to retrieve the "final quality score" and other identifying information associated with the object 802 to confirm the identity of the object 802. For example, the tag identifier could be transmitted from the reading device 806 to a server 812, which, in turn, submits the tag identifier to a first processor accessible memory device subsystem 814 storing a data record linking the tag identifier and the corresponding "final quality score" and other identifying information. The memory device subsystem 814 returns the data record to the server 812, which, in turn, can pass the data record to the reader 806, which stores the data record in its memory device subsystem 810 ("second processor accessible memory device subsystem). The "final quality score" and other identifying information associated with the object can be output via display or printing from the reading device 806 or other communicatively connected device to a user, who can refer to such output information to verify the identity of the object 802.

As stated above, the specific system 800 shown in FIG. 8 is a specific implementation of the system 100 shown in FIG. 1. Although the implementation of FIG. 8 can be advantageous in certain situations, the invention includes other implementations. In relation to FIG. 1, the data processing device system 110 can include the tag-reading device 806, the server 812, or both the hand-held device 806 and the server 812. In some embodiments, the tag 804 includes data processing capabilities, and in these cases, the tag can be considered part of the data processing device system 110 of FIG. 1. Further, the first and second processor accessible memory device subsystems 814, 810 can be considered part of the processor-accessible memory device system 140 in FIG. 1. In some embodiments, the tag 804 includes data storage capabilities. In these cases, the tag 804 can also be considered part of the processor-accessible memory device system 140 in FIG. 1.

It is to be understood that the exemplary embodiments are merely illustrative of the present invention and that many variations of the above-described embodiments can be devised by one skilled in the art without departing from the scope of the invention. For example, although embodiments of the present invention are described as generating multiple intermediate quality scores before generating a final quality score, such intermediate quality scores need not be generated and a final quality score can be generated in a single step. In addition, although embodiments of the present invention are described as generating a single quality score indicating a condition of an object, multiple quality scores can be generated for a single object, each score indicating either a different condition or a condition of a different portion of an object. It is therefore intended that all such variations be included within the scope of the following claims and their equivalents.

TABLE I

Example Weighting Factor Database

| Flaw Type | Severity Type | Size | Location | Weighting Factor |
|---|---|---|---|---|
| Printing | Minor | | | 10 |
| | Major | | | 20 |
| Fold Line | Some Wear | | | 20 |
| | Heavy Wear | | | 200 |
| | Separation | .25 Inch | | 50 |
| | Separation | .5 inch | | 60 |
| | Separation | .75 inch | | 70 |
| | Separation | 1 inch | | 80 |
| | Separation | 1.5 inch | | 90 |
| | Separation | 2 inch | | 100 |
| | Separation | 2.5 inch | | 110 |
| | Separation | 3 inch | | 120 |
| | Separation | 3.5 inch | | 130 |
| | Separation | 4 inch | | 140 |
| | Separation | 4.5 inch | | 150 |
| | Separation | 5 inch | | 160 |
| | Separation | 5.5 inch | | 170 |
| | Separation | 6 inch | | 180 |
| | Separation | 6.5 inch | | 190 |
| | Separation | 7 inch | | 200 |
| | Separation | 7.5 inch | | 210 |
| | Separation | 8 inch | | 220 |
| | Separation | 8.5 inch | | 230 |
| | Separation | 9 inch | | 240 |
| | Separation | >9 inch | | 250 |
| Tear | | .125 inch | Border Area | 5 |
| | | .25 inch | Border Area | 10 |
| | | .5 inch | Border Area | 20 |
| | | .75 inch | Border Area | 30 |
| | | 1 inch | Border Area | 40 |
| | | 2 inch | Border Area | 80 |
| | | 3 inch | Border Area | 120 |
| | | 4 inch | Border Area | 160 |
| | | 5 inch | Border Area | 200 |
| | | 6 inch | Border Area | 240 |
| | | 7 inch | Border Area | 280 |
| | | 8 inch | Border Area | 320 |
| | | 9 inch | Border Area | 360 |
| | | 10 inch | Border Area | 400 |
| | | 11 inch | Border Area | 440 |
| | | 12 inch | Border Area | 480 |
| | | >12 inch | Border Area | 520 |
| | | .125 inch | Image Area | 7.5 |
| | | .25 inch | Image Area | 15 |
| | | .5 inch | Image Area | 30 |
| | | .75 inch | Image Area | 45 |
| | | 1 inch | Image Area | 60 |
| | | 2 inch | Image Area | 120 |
| | | 3 inch | Image Area | 180 |
| | | 4 inch | Image Area | 240 |
| | | 5 inch | Image Area | 300 |
| | | 6 inch | Image Area | 360 |
| | | 7 inch | Image Area | 420 |
| | | 8 inch | Image Area | 480 |
| | | 9 inch | Image Area | 540 |
| | | 10 inch | Image Area | 600 |
| | | 11 inch | Image Area | 660 |
| | | 12 inch | Image Area | 720 |
| | | >12 inch | Image Area | 780 |
| Holes | | | Border | 10 |
| | | | Image Area | 15 |
| | | | Actor Eyes | 50 |
| Compression Mark | Minor | | | 10 |
| | Major | | | 20 |
| Restoration | Professional Restoration | | | 10 |
| | Border Repair | | | 20 |
| | Tear Repair | | | 30 |
| | Paper Replacement | | | 40 |
| | Color Touch Up - Professional | | | 50 |
| | Color Touch Up - Amature | | | 60 |
| Border Chip | | .25 inch | | 10 |
| Fading | Sun Fading - 1 Shade Variance | | | 30 |
| | Sun Fading - 2 Shade Variance | | | 40 |
| | Sun Fading - 3 Shade Variance | | | 50 |
| | Sun Fading - 4 Shade Variance | | | 60 |
| | Sun Fading - 5 Shade Variance | | | 70 |
| | Sun Fading >5 Shade Variance | | | 80 |
| Tape | Repair Residue/Stain/Bleed Through | | Front | 30 |
| | | | Back | 30 |
| | Residue/Stain | | Border | 20 |
| | Residue/Stain | | Image Area | 60 |
| Edge Wear | | 1 inch | | 10 |
| | | 2 inch | | 20 |
| | | 3 inch | | 30 |
| | | 4 inch | | 40 |
| | | 5 inch | | 50 |
| | | 6 inch | | 60 |
| | | 7 inch | | 70 |
| | | 8 inch | | 80 |
| | | 9 inch | | 90 |
| | | 10 inch | | 100 |
| | | 11 inch | | 110 |
| | | 12 inch | | 120 |
| | | >12 inch | | 999 |
| Writing | No Bleed Through | | Back | 10 |
| | Bleed Through - Slight | | Back | 20 |
| | Bleed Through - Heavy | | Back | 60 |
| | Autograph | | Front | 0 |
| | Writing Normal | | Border | 30 |
| | Writing Above Normal | | Border | 45 |
| | Writing Above Normal | | Front/image | 90 |
| | Writing WC Normal | | White Area | 40 |
| | Stenciled WC | | White Area | 30 |
| Creases/Wrinkles | | .5 inch | Corner | 5 |
| | | <5% | | 20 |
| | | 5% | | 35 |
| | | 10% | | 40 |
| | | 15% | | 45 |
| | | 20% | | 50 |
| | | 25% | | 55 |
| | | 30% | | 60 |
| | | 35% | | 65 |
| | | 40% | | 70 |
| | | 45% | | 75 |

TABLE I-continued

Example Weighting Factor Database

| Flaw Type | Severity Type | Size | Location | Weighting Factor |
|---|---|---|---|---|
| | | 50% | | 80 |
| | | >50% | | 95 |
| Paper Loss | | .125 inch | Border | 5 |
| | | .25 inch | Border | 10 |
| | | .5 inch | Border | 20 |
| | | .75 inch | Border | 30 |
| | | 1 inch | Border | 40 |
| | | 1.5 inch | Border | 50 |
| | | 2 inch | Border | 60 |
| | | 2.5 inch | Border | 70 |
| | | 3 inch | Border | 80 |
| | | 3.5 inch | Border | 90 |
| | | 4 inch | Border | 100 |
| | | 4.5 inch | Border | 110 |
| | | 5 inch | Border | 120 |
| | | 5.5 inch | Border | 130 |
| | | 6 inch | Border | 140 |
| | | 6.5 inch | Border | 150 |
| | | 7 inch | Border | 160 |
| | | >7 inch | Border | 170 |
| | | Trimmed | Border | 240 |
| | | .25 inch | Image Area | 30 |
| | | .5 inch | Image Area | 60 |
| | | .75 inch | Image Area | 90 |
| | | 1 inch | Image Area | 120 |
| | | 1.5 inch | Image Area | 150 |
| | | 2 inch | Image Area | 180 |
| | | 2.5 inch | Image Area | 210 |
| | | 3 inch | Image Area | 240 |
| | | 3.5 inch | Image Area | 270 |
| | | 4 inch | Image Area | 300 |
| | | 4.5 inch | Image Area | 330 |
| | | 5 inch | Image Area | 360 |
| | | 5.5 inch | Image Area | 390 |
| | | 6 inch | Image Area | 420 |
| | | 6.5 inch | Image Area | 450 |
| | | 7 inch | Image Area | 480 |
| | | >7 inch | Image Area | 510 |
| Backing | Linen | | | 10 |
| | Paper | | | 10 |
| Stain/ Smudge/ Censor Stamp | | .125 inch | Border | 5 |
| | | .25 inch | Border | 7.5 |
| | | .5 inch | Border | 10 |
| | | .75 inch | Border | 20 |
| | | 1 inch | Border | 30 |
| | | 1.5 inch | Border | 40 |
| | | 2 inch | Border | 50 |
| | | 2.5 inch | Border | 60 |
| | | 3 inch | Border | 70 |
| | | 3.5 inch | Border | 80 |
| | | 4 inch | Border | 90 |
| | | 4.5 inch | Border | 100 |
| | | 5 inch | Border | 110 |
| | | 5.5 inch | Border | 120 |
| | | 6 inch | Border | 130 |
| | | >6 inch | Border | 140 |
| | | /.5 inch | Image Area | 20 |
| | | .75 inch | Image Area | 40 |
| | | 1 inch | Image Area | 60 |
| | | 1.5 inch | Image Area | 80 |
| | | 2 inch | Image Area | 100 |
| | | 2.5 inch | Image Area | 120 |
| | | 3 inch | Image Area | 140 |
| | | 3.5 inch | Image Area | 160 |
| | | 4 inch | Image Area | 180 |
| | | 4.5 inch | Image Area | 200 |
| | | 5 inch | Image Area | 220 |
| | | 5.5 inch | Image Area | 240 |
| | | 6 inch | Image Area | 260 |
| | | >6 inch | Image Area | 280 |
| Water/ Dampness Stain | | .5 inch | Border | 5 |
| | | 1 inch | Border | 10 |
| | | 2 inch | Border | 20 |
| | | 3 inch | Border | 30 |
| | | 4 inch | Border | 40 |
| | | 5 inch | Border | 50 |
| | | 6 inch | Border | 60 |
| | | 7 inch | Border | 70 |
| | | 8 inch | Border | 80 |
| | | >8 inch | Border | 90 |
| | | 0.5 inch | Image Area | 15 |
| | | 1 inch | Image Area | 30 |
| | | 2 inch | Image Area | 60 |
| | | 3 inch | Image Area | 90 |
| | | 4 inch | Image Area | 120 |
| | | 5 inch | Image Area | 150 |
| | | 6 inch | Image Area | 180 |
| | | 7 inch | Image Area | 210 |
| | | 8 inch | Image Area | 240 |
| | | >8 inch | Image Area | 270 |
| Scratches | | 0.125 inch | | 5 |
| | | .25 inch | | 10 |
| | | .5 inch | | 20 |
| | | .75 inch | | 30 |
| | | 1 inch | | 40 |
| | | 2 inch | | 80 |
| | | 3 inch | | 120 |
| | | 4 inch | | 160 |
| | | 5 inch | | 200 |
| | | 6 inch | | 240 |
| | | 7 inch | | 280 |
| | | 8 inch | | 320 |
| | | 9 inch | | 360 |
| | | 10 inch | | 400 |
| | | 11 inch | | 440 |
| | | 12 inch | | 480 |
| | | >12 inch | | 520 |
| Unusual Paper Aging | Yellowing | | | 10 |
| | Slight Brown | | | 20 |
| | Brown | | | 30 |
| | Brittleness/Flaking | | | 40 |
| Surface Wear | | 0.125 inch | | 5 |
| | | .25 inch | | 10 |
| | | .5 inch | | 20 |
| | | .75 inch | | 30 |
| | | 1 inch | | 40 |
| | | 2 inch | | 80 |
| | | 3 inch | | 120 |
| | | 4 inch | | 160 |
| | | 5 inch | | 200 |
| | | 6 inch | | 240 |
| | | 7 inch | | 280 |
| | | 8 inch | | 320 |
| | | 9 inch | | 360 |
| | | 10 inch | | 400 |
| | | 11 inch | | 440 |
| | | 12 inch | | 480 |
| | | >12 inch | | 520 |

TABLE II(A)

Example Grading Matrix

| Grade # | Grade | Printing | Fold Line | Tear | Holes | Compression Mark |
|---|---|---|---|---|---|---|
| 10.0 | Mint | 0 | 10 | 0 | 0 | 0 |
| 9.5 | Near Mint | 10 | 20 | 10 | 0 | 10 |
| 9.0 | Very Fine + | 10 | 120 | 30 | 80 | 20 |
| 8.5 | Very Fine | 20 | 200 | 40 | 150 | 40 |
| 8.0 | Very Fine − | 30 | 300 | 40 | 300 | 60 |
| 7.5 | Fine + | 40 | 400 | 80 | 380 | 80 |
| 7.0 | Fine | 50 | 500 | 130 | 450 | 100 |
| 6.5 | Fine − | 60 | 600 | 240 | 520 | 140 |
| 6.0 | Very Good + | 70 | 720 | 310 | 580 | 180 |
| 5.5 | Very Good | 80 | 840 | 310 | 640 | 220 |
| 5.0 | Very Good − | 90 | 960 | 480 | 700 | 260 |
| 4.5 | Good + | 100 | 1100 | 600 | 760 | 300 |
| 4.0 | Good | 110 | 10000 | 750 | 820 | 999 |
| 3.5 | Good − | 120 | 10000 | 900 | 900 | 999 |
| 3.0 | Fair + | 130 | 10000 | 1100 | 1100 | 999 |
| 2.5 | Fair | 140 | 10000 | 1300 | 1500 | 999 |
| 2.0 | Fair − | 150 | 10000 | 1600 | 2000 | 999 |
| 1.0 | Poor | 1000000 | 1000000 | 1000000 | 1000000 | 1000000 |

TABLE II(B)

Example Grading Matrix (Continued)

| Grade # | Restoration | Border Chip | Fading | Tape | Edge Wear | Writing | Creases/ Wrinkles |
|---|---|---|---|---|---|---|---|
| 10.0 | 0 | 0 | 0 | 0 | 0 | 0 | 0 |
| 9.5 | 0 | 10 | 0 | 5 | 10 | 10 | 0 |
| 9.0 | 10 | 20 | 0 | 10 | 20 | 20 | 10 |
| 8.5 | 20 | 40 | 0 | 15 | 30 | 20 | 30 |
| 8.0 | 30 | 60 | 0 | 20 | 40 | 30 | 40 |
| 7.5 | 40 | 80 | 0 | 30 | 60 | 30 | 50 |
| 7.0 | 50 | 100 | 0 | 60 | 80 | 40 | 60 |
| 6.5 | 60 | 150 | 0 | 90 | 100 | 40 | 70 |
| 6.0 | 90 | 190 | 30 | 120 | 120 | 50 | 80 |
| 5.5 | 120 | 230 | 30 | 150 | 999 | 50 | 80 |
| 5.0 | 150 | 270 | 40 | 190 | 999 | 60 | 90 |
| 4.5 | 180 | 320 | 40 | 230 | 999 | 60 | 999 |
| 4.0 | 210 | 360 | 50 | 270 | 999 | 90 | 999 |
| 3.5 | 240 | 400 | 50 | 310 | 999 | 120 | 999 |
| 3.0 | 270 | 440 | 60 | 350 | 999 | 160 | 999 |
| 2.5 | 310 | 480 | 60 | 400 | 999 | 200 | 999 |
| 2.0 | 350 | 600 | 70 | 450 | 999 | 300 | 999 |
| 1.0 | 1000000 | 1000000 | 1000000 | 1000000 | 1000000 | 1000000 | 1000000 |

TABLE II(C)

Example Grading Matrix (Continued)

| Grade # | Paper Loss | Backing | Stain/ Smudge/ Censor Stamp | Water/ Dampness Stain | Scratches | Unusual Paper Aging | Surface Wear |
|---|---|---|---|---|---|---|---|
| 10.0 | 0 | 0 | 0 | 0 | 0 | 0 | 0 |
| 9.5 | 0 | 0 | 0 | 0 | 10 | 0 | 10 |
| 9.0 | 0 | 10 | 20 | 20 | 20 | 0 | 20 |
| 8.5 | 10 | 10 | 50 | 50 | 30 | 10 | 30 |
| 8.0 | 20 | 10 | 100 | 100 | 40 | 10 | 40 |
| 7.5 | 50 | 10 | 200 | 200 | 80 | 10 | 80 |
| 7.0 | 90 | 10 | 300 | 300 | 120 | 20 | 120 |
| 6.5 | 100 | 10 | 350 | 350 | 160 | 20 | 160 |
| 6.0 | 150 | 10 | 400 | 400 | 200 | 20 | 200 |

TABLE II(C)-continued

Example Grading Matrix (Continued)

| Grade # | Paper Loss | Backing | Stain/ Smudge/ Censor Stamp | Water/ Dampness Stain | Scratches | Unusual Paper Aging | Surface Wear |
|---|---|---|---|---|---|---|---|
| 5.5 | 180 | 10 | 450 | 450 | 240 | 20 | 240 |
| 5.0 | 210 | 10 | 500 | 500 | 360 | 30 | 195 |
| 4.5 | 240 | 10 | 550 | 550 | 450 | 30 | 225 |
| 4.0 | 280 | 10 | 600 | 600 | 520 | 30 | 520 |
| 3.5 | 310 | 10 | 650 | 650 | 600 | 30 | 600 |
| 3.0 | 340 | 10 | 700 | 700 | 700 | 30 | 700 |
| 2.5 | 420 | 10 | 750 | 750 | 900 | 40 | 900 |
| 2.0 | 520 | 10 | 800 | 800 | 1300 | 40 | 1300 |
| 1.0 | 1000000 | 1000000 | 1000000 | 1000000 | 1000000 | 1000000 | 1000000 |

What is claimed is:

1. A method for evaluating an object, the method implemented at least in part by a data processing device system, and the method comprising the steps of:
receiving input comprising indications of: a plurality of flaws present on or in the object, a flaw type for each of the flaws, and a severity for each of the flaws;
determining weighting factors associated with the plurality of flaws, the weighting factors dependent at least on the seventies of the flaws;
determining a quality-score indicating a condition of the object based at least on at least some of the weighting factors and the flaw types for at least some of the flaws; and
storing the quality-score in a processor accessible memory device system,
wherein the severity of at least some of the flaws indicates at least a severity type for each of the at least some of the flaws, the severity type being different from the flaw type and being different from a flaw location for each of the at least some of the flaws,
wherein the method further comprises the step of determining a plurality of intermediate quality scores,
wherein each of the steps is performed at least in part by a data processing device of the data processing device system,
wherein one of the intermediate quality scores indicates a preliminary assessment of the condition of the object,
wherein the quality score is determined based at least on at least some of the weighting factors, the flaw types for at least some of the flaws, and the intermediate quality scores,
wherein a first of the intermediate quality scores is determined based at least on an assessment of damage to the object due to flaws having a particular flaw type, the particular flaw type being one of the flaw types that presents the most damage to the object as compared to the others of the flaw types,
wherein a second of the intermediate quality scores is determined based at least on the first of the intermediate quality scores and a flaw type not factored into the first of the intermediate quality scores and determined to present the next-most damage to the object after the particular flaw type, and
wherein the object is a movie poster.

2. The method of claim 1, wherein the number of intermediate quality scores is inversely proportional to object quality.

3. The method of claim 1, wherein the severity of the at least some of the flaws indicates at least the flaw location for each of the at least some of the flaws, and wherein the weighting factors associated with the at least some of the flaws each are dependent at least on the corresponding flaw location.

4. The method of claim 1, wherein the severity of the at least some of the flaws indicates at least a flaw size for each of the at least some of the flaws, and wherein the weighting factors associated with the at least some of the flaws each are dependent at least on the corresponding flaw size.

5. The method of claim 1, wherein the severity of the at least some of the flaws that indicates the severity type also indicates at least a flaw size corresponding to the respective severity type for each of the at least some of the flaws, and wherein the weighting factors associated with the at least some of the flaws each are dependent at least on the corresponding combination of severity type and flaw size.

6. The method of claim 1, wherein the severity of the at least some of the flaws that indicates a severity type also indicates at least the flaw location, which corresponds to the respective severity type, for each of the at least some of the flaws, and wherein the weighting factors associated with the at least some of the flaws each are dependent at least on the corresponding combination of severity type and flaw location.

7. The method of claim 5, wherein the severity of the at least some of the flaws that indicates a severity type and a flaw size also indicates at least the flaw location, which corresponds to the respective severity type and flaw size, for each of the at least some of the flaws, and wherein the weighting factors associated with the at least some of the flaws each are dependent at least on the corresponding combination of severity type, flaw size, and flaw location.

8. The method of claim 1, further comprising the steps of generating a report identifying at least all of the flaws and their corresponding weighting factors, flaw types, and severities; and storing the report in the processor-accessible memory-device system.

9. The method of claim 1, further comprising the steps of associating the quality score with a word-based score; and storing the word-based score in the processor-accessible memory-device system.

10. The method of claim 1, wherein the flaw types are selected from a set of available flaw types stored in a database, and wherein the method further comprises the steps of:
receiving second input comprising an indication that an existing one of the available flaw types should be changed or a new available flaw type should be added to the set of available flaw types; and
changing the existing one of the available flaw types in the database or adding the new available flaw type to the database in accordance with and in response to receiving the second input.

11. The method of claim 1, wherein the step of determining the weighting factors comprises retrieving the weighting factors from a database, and wherein the method further comprises the steps of:
- receiving second input comprising an indication that a particular one of the weighting factors in the database should be changed; and
- changing the particular one of the weighting factors in accordance with and in response to receiving the second input.

12. The method of claim 3, wherein the flaw locations are selected from a set of available flaw locations stored in a database, and wherein the method further comprises the steps of:
- receiving second input comprising an indication that an existing one of the available flaw locations should be changed or a new available flaw location should be added to the set of available flaw locations; and
- changing the existing one of the available flaw locations in the database or adding the new available flaw location to the database in accordance with and in response to receiving the second input.

13. The method of claim 4, wherein the flaw sizes are selected from a set of available flaw sizes stored in a database, and wherein the method further comprises the steps of:
- receiving second input comprising an indication that an existing one of the available flaw sizes should be changed or a new available flaw size should be added to the set of available flaw sizes; and
- changing the existing one of the available flaw sizes in the database or adding the new available flaw size to the database in accordance with and in response to receiving the second input.

14. The method of claim 1, wherein the severity types are selected from a set of available severity types stored in a database, and wherein the method further comprises the steps of:
- receiving second input comprising an indication that an existing one of the available severity types should be changed or a new available severity type should be added to the set of available severity types; and
- changing the existing one of the available severity types in the database or adding the new available severity type to the database in accordance with and in response to receiving the second input.

15. The method of claim 1, wherein the step of determining the plurality of intermediate quality scores comprises determining the intermediate quality scores based upon discount factors stored in a database, and wherein the method further comprises the steps of:
- receiving second input comprising an indication that one of the discount factors should be changed; and
- changing the one of the discount factors in the database in accordance with and in response to receiving the second input.

16. A non-transitory processor-accessible memory device system storing processor-executable instructions, the processor-executable instructions comprising:
- reception instructions configured to cause a data processing device system to receive input comprising indications of: a plurality of flaws present on or in an object, a flaw type for each of the flaws, and a severity for each of the flaws;
- weighting factor determination instructions configured to cause the data processing device system to determine weighting factors associated with the plurality of flaws, the weighting factors dependent at least on the severities of the flaws;
- quality score determination instructions configured to cause the data processing device system to determine a quality-score indicating a condition of the object based at least on at least some of the weighting factors and the flaw types for at least some of the flaws; and
- storage instructions configured to cause the data processing device system to store the quality-score in the non-transitory processor accessible memory device system,
- wherein the severity of at least some of the flaws indicates at least a severity type for each of the at least some of the flaws, the severity type being different from the flaw type and being different from a flaw location for each of the at least some of the flaws,
- wherein the quality score determination instructions are configured to cause the data processing device system to determine a plurality of intermediate quality scores,
- wherein one of the intermediate quality scores indicates a preliminary assessment of the condition of the object,
- wherein the quality score determination instructions are configured to cause the data processing device system to determine the quality score based at least on at least some of the weighting factors, the flaw types for at least some of the flaws, and the intermediate quality scores.
- wherein the quality score determination instructions are configured to cause the data processing device system to determine a first of the intermediate quality scores based at least on an assessment of damage to the object due to flaws having a particular flaw type, the particular flaw type being one of the flaw types that presents the most damage to the object as compared to the others of the flaw types,
- wherein the quality score determination instructions are configured to cause the data processing device system to determine a second of the intermediate quality scores based at least on the first of the intermediate quality scores and a flaw type not factored into the first of the intermediate quality scores and determined to present the next-most damage to the object after the particular flaw type, and
- wherein the object is a movie poster.

17. The non-transitory processor-accessible memory device system of claim 16, wherein the number of intermediate quality scores is inversely proportional to object quality.

18. The non-transitory processor-accessible memory device system of claim 16, wherein the severity of the at least some of the flaws indicates at least the flaw location for each of the at least some of the flaws, and wherein the weighting factors associated with the at least some of the flaws each are dependent at least on the corresponding flaw location.

19. The non-transitory processor-accessible memory device system of claim 16, wherein the severity of the at least some of the flaws indicates at least a flaw size for each of the at least some of the flaws, and wherein the weighting factors associated with the at least some of the flaws each are dependent at least on the corresponding flaw size.

20. The non-transitory processor-accessible memory device system of claim 16, wherein the severity of the at least some of the flaws that indicates the severity type also indicates at least a flaw size corresponding to the respective severity type for each of the at least some of the flaws, and wherein the weighting factors associated with the at least some of the flaws each are dependent at least on the corresponding combination of severity type and flaw size.

21. The non-transitory processor-accessible memory device system of claim 16, wherein the severity of the at least some of the flaws that indicates a severity type also indicates at least the flaw location, which corresponds to the respective severity type, for each of the at least some of the flaws, and wherein the weighting factors associated with the at least some of the flaws each are dependent at least on the corresponding combination of severity type and flaw location.

22. The non-transitory processor-accessible memory device system of claim 20, wherein the severity of the at least some of the flaws that indicates a severity type and a flaw size also indicates at least the flaw location, which corresponds to the respective severity type and flaw size, for each of the at least some of the flaws, and wherein the weighting factors associated with the at least some of the flaws each are dependent at least on the corresponding combination of severity type, flaw size, and flaw location.

23. The non-transitory processor-accessible memory device system of claim 16, wherein the processor-executable instructions comprise generation instructions configured to cause the data processing device system to (a) generate a report identifying at least all of the flaws and their corresponding weighting factors, flaw types, and severities, and (b) store the report in the non-transitory processor-accessible memory-device system.

24. The non-transitory processor-accessible memory device system of claim 16, wherein the processor-executable instructions comprise instructions configured to cause the data processing device system to (a) associate the quality score with a word-based score, and (b) store the word-based score in the non-transitory processor-accessible memory-device system.

25. The non-transitory processor-accessible memory device system of claim 16,
   wherein the processor-executable instructions comprise selection instructions configured to cause the data processing device system to select the flaw types from a set of available flaw types stored in a database,
   wherein the reception instructions are configured to cause the data processing device system to receive second input comprising an indication that an existing one of the available flaw types should be changed or a new available flaw type should be added to the set of available flaw types, and
   wherein the processor-executable instructions comprise instructions configured to cause the data processing device system to change the existing one of the available flaw types in the database or add the new available flaw type to the database in accordance with and in response to the second input.

26. The non-transitory processor-accessible memory device system of claim 16,
   wherein the weighting factor determination instructions are configured to cause the data processing device system to retrieve the weighting factors from a database,
   wherein the reception instructions are configured to cause the data processing device system to receive second input comprising an indication that a particular one of the weighting factors in the database should be changed, and
   wherein the processor-executable instructions comprise instructions configured to cause the data processing device system to change the particular one of the weighting factors in accordance with and in response to the second input.

27. The non-transitory processor-accessible memory device system of claim 18,
   wherein the processor-executable instructions comprise selection instructions configured to cause the data processing device system to select the flaw locations from a set of available flaw locations stored in a database,
   wherein the reception instructions are configured to cause the data processing device system to receive second input comprising an indication that an existing one of the available flaw locations should be changed or a new available flaw location should be added to the set of available flaw locations, and
   wherein the processor-executable instructions comprise instructions configured to cause the data processing device system to change the existing one of the available flaw locations in the database or add the new available flaw location to the database in accordance with and in response to the second input.

28. The non-transitory processor-accessible memory device system of claim 19,
   wherein the processor-executable instructions comprise selection instructions configured to cause the data processing device system to select the flaw sizes from a set of available flaw sizes stored in a database,
   wherein the reception instructions are configured to cause the data processing device system to receive second input comprising an indication that an existing one of the available flaw sizes should be changed or a new available flaw size should be added to the set of available flaw sizes, and
   wherein the processor-executable instructions comprise instructions configured to cause the data processing device system to change the existing one of the available flaw sizes in the database or add the new available flaw size to the database in accordance with and in response to the second input.

29. The non-transitory processor-accessible memory device system of claim 16,
   wherein the processor-executable instructions comprise selection instructions configured to cause the data processing device system to select the severity types from a set of available severity types stored in a database,
   wherein the reception instructions are configured to cause the data processing device system to receive second input comprising an indication that an existing one of the available severity types should be changed or a new available severity type should be added to the set of available severity types, and
   wherein the processor-executable instructions comprise instructions configured to cause the data processing device system to change the existing one of the available severity types in the database or add the new available severity type to the database in accordance with and in response to the second input.

30. The non-transitory processor-accessible memory device system of claim 16,
   wherein the quality score determination instructions are configured to cause the data processing device system to determine the intermediate quality scores based upon discount factors stored in a database,
   wherein the reception instructions are configured to cause the data processing device system to receive second input comprising an indication that one of the discount factors should be changed, and
   wherein the processor-executable instructions comprise instructions configured to cause the data processing device system to change the one of the discount factors in the database in accordance with and in response to the second input.

31. A system comprising:
a data processing device system; and
a processor-accessible memory device system communicatively connected to the data processing device system and storing processor-executable instructions executable by the data processing device system, wherein the processor-executable instructions comprise:
reception instructions for receiving input comprising indications of: a plurality of flaws present on or in an object, a flaw type for each of the flaws, and a severity for each of the flaws;
weighting factor instructions for determining weighting factors associated with the plurality of flaws, the weighting factors dependent at least on the severities of the flaws;
quality score determination instructions for determining a quality-score indicating a condition of the object based at least on at least some of the weighting factors and the flaw types for at least some of the flaws; and
storage instructions for storing the quality-score in the processor accessible memory device system,
wherein the severity of at least some of the flaws indicates at least a severity type for each of the at least some of the flaws, the severity type being different from the flaw type and being different from a flaw location for each of the at least some of the flaws,
wherein the quality score determination instructions include instructions for determining a plurality of intermediate quality scores,
wherein one of the intermediate quality scores indicates a preliminary assessment of the condition of the object,
wherein the quality score determination instructions include instructions for determining the quality score based at least on at least some of the weighting factors, the flaw types for at least some of the flaws, and the intermediate quality scores,
wherein the quality score determination instructions include instructions for determining a first of the intermediate quality scores based at least on an assessment of damage to the object due to flaws having a particular flaw type, the particular flaw type being one of the flaw types that presents the most damage to the object as compared to the others of the flaw types,
wherein the quality score determination instructions include instructions for determining a second of the intermediate quality scores based at least on the first of the intermediate quality scores and a flaw type not factored into the first of the intermediate quality scores and determined to present the next-most damage to the object after the particular flaw type, and
wherein the object is a movie poster.

32. The system of claim 31, wherein the number of intermediate quality scores is inversely proportional to object quality.

33. The system of claim 31, wherein the severity of the at least some of the flaws indicates at least the flaw location for each of the at least some of the flaws, and wherein the weighting factors associated with the at least some of the flaws each are dependent at least on the corresponding flaw location.

34. The system of claim 31, wherein the severity of the at least some of the flaws indicates at least a flaw size for each of the at least some of the flaws, and wherein the weighting factors associated with the at least some of the flaws each are dependent at least on the corresponding flaw size.

35. The system of claim 31, wherein the severity of the at least some of the flaws that indicates the severity type also indicates at least a flaw size corresponding to the respective severity type for each of the at least some of the flaws, and wherein the weighting factors associated with the at least some of the flaws each are dependent at least on the corresponding combination of severity type and flaw size.

36. The system of claim 31, wherein the severity of the at least some of the flaws that indicates a severity type also indicates at least the flaw location, which corresponds to the respective severity type, for each of the at least some of the flaws, and wherein the weighting factors associated with the at least some of the flaws each are dependent at least on the corresponding combination of severity type and flaw location.

37. The system of claim 35, wherein the severity of the at least some of the flaws that indicates a severity type and a flaw size also indicates at least the flaw location, which corresponds to the respective severity type and flaw size, for each of the at least some of the flaws, and wherein the weighting factors associated with the at least some of the flaws each are dependent at least on the corresponding combination of severity type, flaw size, and flaw location.

38. The system of claim 31, wherein the processor-executable instructions comprise generation instructions for generating a report identifying at least all of the flaws and their corresponding weighting factors, flaw types, and severities, and storing the report in the processor-accessible memory-device system.

39. The system of claim 31, wherein the processor-executable instructions comprise instructions for associating the quality score with a word-based score, and storing the word-based score in the processor-accessible memory-device system.

40. The system of claim 31,
wherein the processor-executable instructions comprise selection instructions for selecting the flaw types from a set of available flaw types stored in a database,
wherein the reception instructions include instructions for receiving second input comprising an indication that an existing one of the available flaw types should be changed or a new available flaw type should be added to the set of available flaw types, and
wherein the processor-executable instructions comprise instructions for changing the existing one of the available flaw types in the database or adding the new available flaw type to the database in accordance with and in response to the second input.

41. The system of claim 31,
wherein the weighting factor determination instructions include instructions for retrieving the weighting factors from a database,
wherein the reception instructions include instructions for receiving second input comprising an indication that a particular one of the weighting factors in the database should be changed, and
wherein the processor-executable instructions comprise instructions for changing the particular one of the weighting factors in accordance with and in response to the second input.

42. The system of claim 33,
wherein the processor-executable instructions comprise selection instructions for selecting the flaw locations from a set of available flaw locations stored in a database,
wherein the reception instructions include instructions for receiving second input comprising an indication that an existing one of the available flaw locations should be changed or a new available flaw location should be added to the set of available flaw locations, and wherein the processor-executable instructions comprise instructions for changing the existing one of the available flaw locations in the database or adding the new available flaw location to the database in accordance with and in response to the second input.

43. The system of claim 34, wherein the processor-executable instructions comprise selection instructions for selecting the flaw sizes from a set of available flaw sizes stored in a database, wherein the reception instructions include instructions for receiving second input comprising an indication that an existing one of the available flaw sizes should be changed or a new available flaw size should be added to the set of available flaw sizes, and wherein the processor-executable instructions comprise instructions for changing the existing one of the available flaw sizes in the database or adding the new available flaw size to the database in accordance with and in response to the second input.

44. The system of claim 31, wherein the processor-executable instructions comprise selection instructions for selecting the severity types from a set of available severity types stored in a database, wherein the reception instructions include instructions for receiving second input comprising an indication that an existing one of the available severity types should be changed or a new available severity type should be added to the set of available severity types, and wherein the processor-executable instructions comprise instructions for changing the existing one of the available severity types in the database or adding the new available severity type to the database in accordance with and in response to the second input.

45. The system of claim 31, wherein the quality score determination instructions include instructions for determining the intermediate quality scores based upon discount factors stored in a database, wherein the reception instructions include instructions for receiving second input comprising an indication that one of the discount factors should be changed, and wherein the processor-executable instructions comprise instructions for changing the one of the discount factors in the database in accordance with and in response to the second input.

* * * * *